(12) United States Patent
Lin et al.

(10) Patent No.: US 7,452,522 B2
(45) Date of Patent: Nov. 18, 2008

(54) EXTRACTION PROCESS FOR REMOVAL OF IMPURITIES FROM AN OXIDIZER PURGE STREAM IN THE SYNTHESIS OF CARBOXYLIC ACID

(75) Inventors: Robert Lin, Kingsport, TN (US); Marcel de Vreede, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 774 days.

(21) Appl. No.: 10/948,591

(22) Filed: Sep. 23, 2004

(65) Prior Publication Data
US 2005/0084432 A1 Apr. 21, 2005

(51) Int. Cl.
*B01D 11/00* (2006.01)
(52) U.S. Cl. .................. 423/658.5; 562/409
(58) Field of Classification Search .......... 423/49, 423/658.5, DIG. 14; 562/409, 412, 414, 562/416, 485–487, 608
See application file for complete search history.

(56) References Cited

U.S. PATENT DOCUMENTS

| | | | |
|---|---|---|---|
| 2,964,559 A | 12/1960 | Burney et al. | |
| 3,840,641 A | 10/1974 | Wampfler et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |
| 4,330,676 A | 5/1982 | Moxham | |
| 4,356,319 A | 10/1982 | Roffia et al. | |
| 4,769,489 A | 9/1988 | Abrams et al. | |
| 4,892,972 A | 1/1990 | Schroeder et al. | |
| 4,914,230 A | 4/1990 | Abrams et al. | |
| 4,939,297 A | 7/1990 | Browder et al. | |
| 5,200,557 A | 4/1993 | Gee et al. | |
| 5,643,468 A | 7/1997 | Ure | |
| 5,676,847 A | 10/1997 | Yamamoto et al. | |
| 5,705,682 A | 1/1998 | Ohkashi et al. | |
| 5,770,765 A | 6/1998 | Ohkashi | |
| 5,840,965 A | 11/1998 | Turner et al. | |
| 5,916,422 A | 6/1999 | Kimura et al. | |
| 5,955,394 A | 9/1999 | Kelly | |
| 6,054,610 A | 4/2000 | Lee et al. | |
| 6,133,476 A | 10/2000 | Lin | |
| 6,153,790 A | 11/2000 | June et al. | |
| 6,562,997 B2 | 5/2003 | Sikkenga et al. | |
| 7,074,954 B2 | 7/2006 | Sheppard et al. | |
| 7,132,566 B2 | 11/2006 | Sumner et al. | |
| 7,273,559 B2 | 9/2007 | Gibson et al. | |
| 7,291,270 B2 | 11/2007 | Gibson et al. | |
| 2001/0041811 A1 | 11/2001 | Sikkenga et al. | |
| 2002/0016500 A1 | 2/2002 | Matsumoto et al. | |
| 2002/0193630 A1 | 12/2002 | Lin et al. | |
| 2004/0225148 A1 | 11/2004 | Isogai et al. | |
| 2004/0244536 A1 | 12/2004 | Lin | |
| 2004/0245176 A1 | 12/2004 | Parker et al. | |
| 2004/0249207 A1 | 12/2004 | Lin et al. | |
| 2004/0249208 A1 | 12/2004 | Lin et al. | |
| 2007/0205153 A1 | 9/2007 | Parker et al. | |
| 2007/0208195 A1 | 9/2007 | Gibson et al. | |
| 2007/0208196 A1 | 9/2007 | Parker et al. | |
| 2007/0208197 A1 | 9/2007 | Gibson et al. | |
| 2007/0208198 A1 | 9/2007 | Parker et al. | |
| 2007/0208199 A1 | 9/2007 | Parker et al. | |
| 2007/0213557 A1 | 9/2007 | Seiki et al. | |

FOREIGN PATENT DOCUMENTS

| | | |
|---|---|---|
| DE | 2131470 A | 6/1970 |
| EP | 0 181 127 A2 | 5/1986 |
| EP | 0 764 627 A1 | 3/1997 |
| EP | 0579715 B1 | 8/1997 |
| GB | 892 766 | 3/1962 |
| GB | 1407705 | 9/1975 |
| GB | 2067563 | 7/1981 |
| JP | 46-14339 B | 4/1971 |
| JP | 49-123191 A | 11/1974 |
| JP | 51-145488 A | 12/1976 |

(Continued)

OTHER PUBLICATIONS

USPTO office action dated Nov. 30, 2006 for copending U.S. Appl. No. 10/975,256.
USPTO office action dated Nov. 30, 2006 for copending U.S. Appl. No. 10/975,252.
USPTO Notice of Allowance dated Jan. 15, 2008 for copending U.S. Appl. No. 10/455,016.
USPTO office action dated Jan. 18, 2007 for copending U.S. Appl. No. 10/455,017.
BHS—Werk Sonthofen, *BHS-Fest Pressure Filter*, 1990, pamphlet, Santhofen, West Germany.
Copending U.S. Appl. No. 10/975,256, filed Oct. 28, 2004.
Copending U.S. Appl. No. 10/975,252, filed Oct. 28, 2004.
Office Action for copending U.S. Appl. No. 10/455,017.
Copending U.S. Appl. No. 11/655,395, filed Jan. 19, 2007, Philip E. Gibson et al.
Copending U.S. Appl. No. 11/655,317, filed Jan. 19, 2007, Philip E. Gibson et al.
Copending U.S. Appl. No. 11/655,396, filed Jan. 19, 2007, Kenny R. Parker et al.

(Continued)

*Primary Examiner*—Steven Bos
(74) *Attorney, Agent, or Firm*—Steven A. Owen; Bernard J. Graves, Jr.

(57) ABSTRACT

Disclosed is a process that relates to the recovery of a metal catalyst from an oxidizer purge stream produced in the synthesis of carboxylic acid, typically terephthalic acid. The process involves the addition of a wash solution to a high temperature molten dispersion to recover the metal catalyst and then subjecting an aqueous mixture or purified aqueous mixture so formed to a single stage extraction to remove organic impurities to produce an extract stream and a raffinate stream comprising the metal catalyst.

14 Claims, 2 Drawing Sheets

FOREIGN PATENT DOCUMENTS

| | | |
|---|---|---|
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | WO 97/30963 A | 8/1997 |
| WO | WO 00/31014 A1 | 6/2000 |
| WO | WO 01/55075 A2 | 8/2001 |

OTHER PUBLICATIONS

USPTO Office Action dated Mar. 14, 2007, for copending U.S. Appl. No. 10/455,016.
USPTO Office Action dated May 11, 2007 for copending U.S. Appl. No. 10/455,017.
USPTO Office Action dated May 14, 2007 for copending U.S. Appl. No. 10/455,018.
USPTO Office Action dated May 17, 2007 for copending U.S. Appl. No. 11/201,512.
USPTO Office Action dated Jul. 6, 2007 for copending U.S. Appl. No. 10/455,016.
USPTO office action dated Jul. 19, 2006 for copending U.S. Appl. No. 10/455,017.
USPTO office action dated Jul. 19, 2006 for copending U.S. Appl. No. 10/455,018.
USPTO office action dated Jul. 19, 2006 for copending U.S. Appl. No. 10/455,016.
Treybal, Robert E., "Stagewise Contact, Single-Stage Extraction," Mass-Transfer Operations, Third Edition, 1980, pp. 490-555, McGraw-Hill Book Company.
Notice of Allowance dated Aug. 1, 2007 for copending U.S. Appl. No. 10/975,252.
Notice of Allowance dated Jul. 18, 2007 for copending U.S. Appl. No. 10/975,256.
Copending U.S. Appl. No. 11/839,575, filed Aug. 16, 2007, Philip Edward Gibson et al.
Copending U.S. Appl. No. 11/839,578, filed Aug. 16, 2007, Philip Edward Gibson et al.
Copending U.S. Appl. No. 11/839,582, filed Aug. 16, 2007, Philip Edward Gibson et al.
Copending U.S. Appl. No. 11/839,573, filed Aug. 16, 2007, Kenny Randolf Parker et al.
Copending U.S. Appl. No. 11/842,413, filed Aug. 21, 2007, Kenny Randolph Parker et al.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
USPTO Office Action dated Sep. 25, 2007 for copending U.S. Appl. No. 11/655,396.
USPTO Office Action dated Sep. 25, 2007 for copending U.S. Appl. No. 11/655,395.
USPTO Office Action dated Oct. 16, 2007 for copending U.S. Appl. No. 11/655,317.
USPTO Notice of Allowance dated Dec. 3, 2007 for copending U.S. Appl. No. 10/455,017.
USPTO Office Action dated Mar. 14, 2008 for copending U.S. Appl. No. 10/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,251, filed Mar. 18, 2008, Robert Lin et al.
Copending U.S. Appl. No. 12/050,253, filed Mar. 18, 2008, Robert Lin et al.
Copending U.S. Appl. No. 12/050,256, filed Mar. 18, 2008, Robert Lin et al.
Copending U.S. Appl. No. 12/050,258, filed Mar. 18, 2008, Robert Lin et al.
USPTO Office Action dated Mar. 4, 2008 for copending U.S. Appl. No. 11/839,575.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO Office Action dated Mar. 5, 2008 for copending U.S. Appl. No. 11/655,396.
USPTO Office Action dated Apr. 25, 2008 for copending U.S. Appl. No. 11/181,214.
USPTO Office Action dated Apr. 4, 2008 for copending U.S. Appl. No. 11/181,449.
USPTO Office Action dated Feb. 14, 2008 for copending U.S. Appl. No. 11/842,469.

EXTRACTION PROCESS FOR REMOVAL OF IMPURITIES FROM AN OXIDIZER PURGE STREAM IN THE SYNTHESIS OF CARBOXYLIC ACID

CROSS-REFERENCE TO RELATED APPLICATIONS

This application claims priority to U.S. Non-Provisional application Ser. No. 10/455,018, filed Jun. 5, 2003, the disclosure of which is incorporated herein by reference in its entirety to the extent it does not contradict statements herein.

FIELD OF INVENTION

This invention relates to the recovery of a metal catalyst from an oxidizer purge stream produced in the synthesis of carboxylic acid, typically terephthalic acid. More particularly, the process involves the addition of a wash solution to a high temperature molten dispersion to recover the metal catalyst and then subjecting an aqueous mixture or purified aqueous mixture so formed to a single stage extraction to remove organic impurities to produce an extract stream and a raffinate stream comprising the metal catalyst. This invention also relates to a process to produce a high boiling point organic impurities stream from an aqueous mixture or a purified aqueous mixture.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities formed as a result of the oxidation of paraxylene.

Terephthalic acid (TPA) is an intermediate in the production of polyesters for plastics and fiber applications. Commercial processes for the manufacture of TPA are often based on the heavy-metal catalyzed oxidation of p-xylene, generally with a bromide promoter in an acetic acid solvent. Due to the limited solubility of TPA in acetic acid under practical oxidation conditions, a slurry of TPA crystals is usually formed in the oxidation reactor. Typically, the TPA oxidizer slurry is withdrawn from the reactor and TPA solids are separated from the oxidizer mother liquor using conventional solid-liquid separation techniques. The oxidizer mother liquor, which contains most of the catalyst and promoter used in the process, is recycled to the oxidation reactor. Aside from the catalyst and promoter, the oxidizer mother liquor also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions formed as a result of the oxidation of p-xylene to terephthalic acid. Patents disclosing the production of terephthalic acid such as U.S. Pat. Nos. 4,158,738 and 3,996,271 are hereby incorporated by reference in their entirety to the extent that they do not contradict statements herein.

The TPA solids undergo a solid-liquid separation wherein fresh solvent is utitlized to displace a major portion of the liquid component of the oxidizer mother liquor. After drying, the TPA solids are contaminated with impurities that were present in the oxidizer mother liquor since these impurities may be incorporated into the TPA solids. Impurities are also present due to occlusions in the TPA crystal structure and due to incomplete removal of the oxidizer mother liquor by the fresh solvent wash.

Many of the impurities in the oxidizer mother liquor stream that are recycled are relatively inert to further oxidation. Such impurities include, for example, isophthalic acid, phthalic acid and trimellitic acid. Impurities, which may undergo further oxidation are also present, such as, for example, 4-carboxybenzaldehyde, p-toluic acid and p-tolualdehyde. Oxidation inert impurities tend to accumulate in the oxidizer mother liquor upon recycle. The concentration of these inert impurities will increase in the oxidizer mother liquor until an equilibrium is reached whereby the rate of removal of each impurity via the TPA product balances with the rate of formation and the rate of addition to the oxidation process. The normal level of impurities in commercial crude TPA makes it unsuitable for direct use in most polymer applications.

Conventionally, crude TPA has been purified either by conversion to a dimethyl ester or by dissolution in water with subsequent hydrogenation over standard hydrogenation catalysts. More recently, secondary oxidative treatments have been used to produce polymer-grade TPA. It is desirable to minimize the concentration of impurities in the mother liquor and thereby facilitate subsequent purification of TPA. In some cases, it is not possible to produce a purified, polymer-grade TPA unless some means for removing impurities from the oxidizer mother liquor stream is utilized.

One technique for impurity removal from a recycle stream commonly used in the chemical processing industry is to draw out or "purge" some portion of the oxidizer mother liquor that is recycled. Typically, the purge stream is simply disposed of or, if economically justified, subjected to various treatments to remove undesired impurities while recovering valuable components. One example is U.S. Pat. No. 4,939,297 herein incorporated by reference in its entirety to the extent it does not contradict statements herein. The amount of purge required for control of impurities is process-dependent; however, a purge amount equal to 10-40%, hereafter known as oxidizer purge stream, of the total oxidizer mother liquor stream is usually sufficient to produce TPA adequate as feedstock for commercial polymer manufacture. In the production of TPA, the percentage purge of the oxidizer mother liquor stream necessary to maintain acceptable impurity concentrations, coupled with the economic value of the metal catalyst and solvent components in the oxidizer purge stream, make simple disposal of the oxidizer purge stream economically unattractive. Thus, there is a need for a process that recovers essentially all of the valuable metal catalysts and acetic acid contained in the oxidizer purge stream while removing a major portion of the impurities present in the oxidizer purge stream. The metal catalyst can be recovered in an active form suitable for reuse by direct recycling to the p-xylene oxidation step.

This invention is a marked improvement over a typical purge process. Some of the advantages are:
1) enhanced operability and reliability due to reduction in plugging potential;
2) reduction in overall energy usage;
3) reduction in the amount of water to the solvent extraction step.

The invention enhances the impurity removal efficacy of the process, and the operability of the process compared to the existing processes. In addition it should be noted that this invention does not just apply to the crude TPA process but any process that produces an oxidizer purge stream where recovery of metal catalyst is needed.

SUMMARY OF THE INVENTION

This invention relates to removal of impurities and the recovery of a metal catalyst from oxidizer purge stream produced in the synthesis of carboxylic acid, typically terephthalic acid. More particularly, the process involves the addition of wash solution to a high temperature molten dispersion to recover the metal catalyst and then subjecting an aqueous mixture or purified aqueous mixture so formed to a single stage extraction to remove organic impurities to produce an extract stream and a raffinate stream. This invention also relates to a process to produce a high boiling point organic impurities stream from an aqueous mixture or a purified aqueous mixture.

It is an object of this invention to provide a process to recover a metal catalyst from an oxidizer purge stream.

It is another object of this invention to provide a process for removal of impurities and the recovery of a metal catalyst from an oxidizer purge stream produced in the synthesis of carboxylic acid.

It is another object of this invention to provide a process to produce a high boiling point organic impurities stream from an aqueous mixture or a purified aqueous mixture.

In a first embodiment of this invention, a process is provided. The process comprises the following steps:
  (a) subjecting an oxidizer purge stream comprising a carboxylic acid, a metal catalyst, impurities, water and a solvent to evaporation in a first evaporator zone to produce a vapor stream and a concentrated purge slurry; and
  (b) subjecting the concentrated purge slurry to evaporation in a second evaporator zone to produce a solvent rich stream and a high temperature molten dispersion; wherein about 95 wt % to about 99 wt % of the solvent and water is removed from the oxidizer purge stream in step (a) and step (b) combined; and wherein the second evaporator zone comprises an evaporator operated at a temperature of about 150° C. to about 200° C.;
  (c) mixing in a mixing zone a wash solution with the high temperature molten dispersion to form an aqueous mixture;
  (d) adding an extraction solvent to the aqueous mixture in an extraction zone to form an extract stream and a raffinate stream; and
  (e) separating the extract stream and the solvent rich stream in a separation zone to form a high boiling point organic impurities stream.

In another embodiment of this invention, a process is provided. The process comprises:
  (a) subjecting an oxidizer purge stream comprising a carboxylic acid, a metal catalyst, impurities, water and a solvent to evaporation in a first evaporator zone to produce a vapor stream and a concentrated purge slurry; and
  (b) subjecting the concentrated purge slurry to evaporation in a second evaporator zone to produce a solvent rich stream and a high temperature molten dispersion; wherein about 95 wt % to about 99 wt % of the solvent and water is removed from the oxidizer purge stream in step (a) and step (b) combined; and wherein the second evaporator zone comprises an evaporator operated at a temperature of about 150° C. to about 200° C.;
  (c) mixing in a mixing zone a wash solution with the high temperature molten dispersion to form an aqueous mixture;
  (d) separating organic impurities from the aqueous mixture in a solid-liquid separation zone to form a purified aqueous mixture;
  (e) adding an extraction solvent to purified aqueous mixture in an extraction zone to form an extract stream and a raffinate stream; and
  (f) separating the extract stream and the solvent rich stream in a separation zone to form a high boiling point organic impurities stream.

These objects, and other objects, will become more apparent to others with ordinary skill in the art after reading this disclosure.

DESCRIPTION OF THE INVENTION

Figure 1:
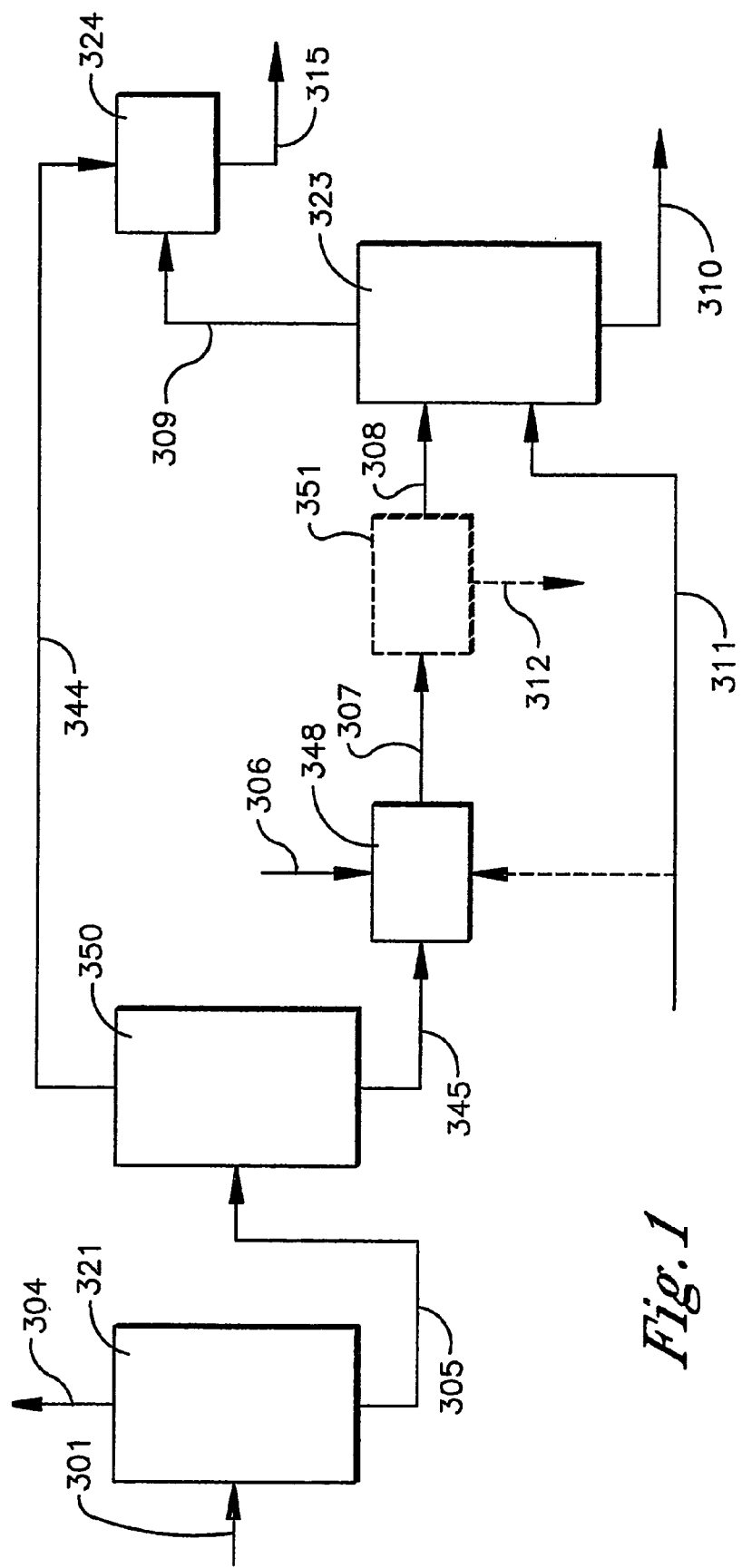
FIG. 1 illustrates different embodiments of the invention wherein a process to recover a metal catalyst and remove impurities from an oxidizer purge stream 301 and a process to produce a high temperature molten dispersion 345 are provided.
Figure 2:
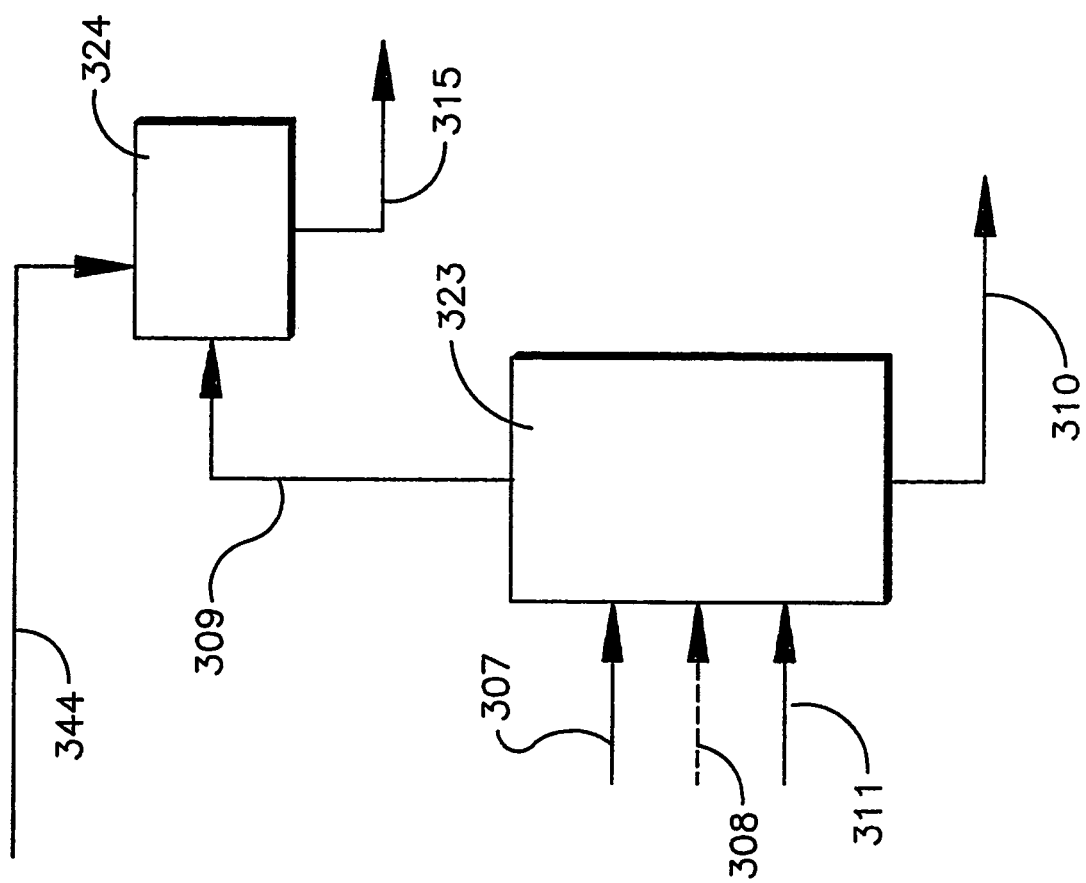
FIG. 2 illustrates different embodiments of the invention wherein a process to produce a high boiling point organic impurities stream 315 from an aqueous mixture 351 or a purified aqueous 308 mixture is provided.

In one embodiment of this invention, a process to recover a metal catalyst and remove impurities from an oxidizer purge stream 301 is provided as shown in FIG. 1. The process comprises the following steps.

Step (a) comprises subjecting an oxidizer purge stream 301 comprising a carboxylic acid, a metal catalyst, impurities, water and a solvent to evaporation in a first evaporator zone 321 to produce a vapor stream 304 and a concentrated purge slurry 305.

The oxidizer purge stream 301 is withdrawn from a carboxylic acid oxidative synthesis process. The oxidizer purge stream 301 serves as the feed stream to the present process. The oxidizer purge stream 301 comprises carboxylic acid, water, a solvent, the metal catalyst and impurities. The impurities comprise organic bromides and corrosion metals. The organic bromides are used as promoters in the oxidation reaction. Examples of corrosion metals are iron and chromium compounds, which inhibit, reduce or entirely destroy the activity of the metal catalyst.

Carboxylic acids include aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic, isophthalic acid, trimellitic acid, naphthalene dicarboxylic acid, and 2,5-diphenyl-terephthalic acid.

Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 8:1 and about 20:1. Throughout the specification acetic acid will be referred to as the solvent. However, it should be appreciated that other suitable solvents, such as those disclosed previously, may also be utilized.

In step (a) of the present process, the oxidizer purge stream 301 is concentrated by conventional means in a first evaporator zone 321 comprising an evaporator to produce a vapor stream 304 and a concentrated purge slurry 305. In an embodiment of the invention, the evaporator is operated at atmospheric or slightly superatmospheric conditions, generally from about 1 atmosphere to about 10 atmospheres. The vapor stream 304 comprises a majority of the water and solvent, and the concentrated purge slurry 305 comprises the remainder of the water and solvent not removed from the oxidizer purge stream 301. In an embodiment of the invention, the evaporation removes about 50 wt % to about 80 wt % of the solvent and water, typically acetic acid and water, which are present in the oxidizer purge stream 301.

Step (b) comprises subjecting the concentrated purge slurry 305 to evaporation in a second evaporator zone 350 to produce a solvent rich stream 344 and a high temperature molten dispersion 345; wherein about 95 wt % to about 99 wt % of the solvent and water is removed from the oxidizer purge stream 301 in step (a) and step (b) combined; and wherein the second evaporator zone 350 comprises an evaporator operated at a temperature of about 150° C. to about 200° C.

The concentrated purge slurry 305 is introduced in the second evaporator zone 350, which comprises at least one evaporator. In an embodiment of the invention, the evaporator is operated at super atmospheric or pressurized conditions, generally from about 1 atmosphere to about 10 atmospheres. The evaporation is conducted at a temperature from about 150° C. to about 220° C.; another range is from about 180° C. to about 200° C. In an embodiment of the invention the combination of evaporators 321 and 350 are operated so as to concentrate the oxidizer purge stream 301 as represented by stream 301 to a condition wherein 95-99 wt % of the solvent, typically acetic acid and water, is removed from the oxidizer purge stream 301.

In an embodiment of the present invention the condition of the high temperature molten dispersion 345 has only enough remaining solvent to provide pumpability. In one embodiment, a typical composition of the the high temperature molten dispersion 345 is shown in Table 1. Generally, the mass composition of the sum total of all compounds shown in Table 1, excluding water and acetic acid, in the high temperature molten dispersion 345 can vary between about 5 wt % to about 80 wt % based on the total weight of the high temperature molten dispersion 345. Another range for the sum total of all compounds shown in Table 1, excluding acetic acid and water, in the high temperature molten dispersion 345 can be all combinations of upper and lower ranges where the lower ranges are 5 wt %, 10 wt %, 15 wt %, 20 wt %, 25 wt %, 30 wt %, 35 wt %, 40 wt % and the upper ranges are 80 wt %, 75 wt %, 70 wt %, 65 wt %, 60 wt %, 55 wt %, 50 wt %, 45 wt % based on the total weight of the high temperature molten dispersion 345. Further, ranges stated in this disclosure and the claims that follow should be understood to disclose the entire range specifically and not just the end point(s). For example, disclosure of the range 0 to 10 should be taken to specifically disclose 2, 2.5, 3.17 and all other number subsumed and not just 0 and 10.

Step (c) comprises mixing in a mixing zone 348 a wash solution 306 with the high temperature molten dispersion 345 to form an aqueous mixture 307.

The high temperature molten dispersion 345 is then subjected to extraction of the metal catalyst in the mixing zone 348 by introduction of a wash solution 306 which can contain water or a water-acetic acid or a wash solution to form an aqueous mixture in stream 307 wherein at least 80% of the metal catalyst is recovered in the aqueous phase of the aqueous mixture 307. Typically, at least 90% of the metal catalyst is recovered in the aqueous phase of the aqueous mixture 307.

The wash solution comprises water and optionally an additional solvent. The solvent can be any substance capable of dissolving the metal catalyst to form a uniformly dispersed solution at the molecular or ionic size level. Typically, the solvent comprises acetic acid, but solvents that have been previously mentioned in step (a) can also be utilized.

The mixing zone 348 comprises a vessel and/or a device or a plurality of vessels or devices wherein there is sufficient residence time for the metal catalyst and/or halogen compounds, such as for example bromine, to dissolve into solution. Examples of such vessels are devices include, but are not limited to, a tank and a stirred or agitated tank. In this step, it is not necessary to completely dissolve the mixture. One method is to utilize only the necessary amount of water to obtain the level of the metal catalyst recovery desired. However, the addition of wash solution 306 also serves to quench the mixture to a temperatures in the range of about 60° C. to about 95° C., another range is about 80° C. to about 90° C. In an embodiment of the invention the quenching is done for about 0.5 to about 4 hours, another range is about 1 to about 2 hours. By this treatment organic bromides are reacted to yield inorganic bromides that are for example, preferentially retained in the aqueous fraction exiting an extractor. The quantity of bromine-containing compounds purged from the system along with the unwanted impurities is thereby minimized. The heat treatment conserves bromides and simplifies disposal of the organic impurities.

The addition of wash solution 306 in the mixing zone 348 not only recovers the metal catalyst in the high temperature molten dispersion 345, but also aids in pumping the aqueous mixture 307. It is desirable to keep the aqueous mixture 307 circulating with an external circulation loop.

In one embodiment, a typical composition of the aqueous mixture is shown in Table 1. Generally, the mass composition of the aqueous mixture 307 in this embodiment generally can vary wherein the mass ratio of water to acetic acid is in the range of about 1:1 to 99:1 and wherein the sum aggregate of isophthalic acid, benzoic acid, 4-carboxybenzaldehyde, and terephthalic acid comprises between about 1000 ppm to about 65 wt % of the total weight of the aqueous mixture 307. Another range can be all combinations of upper and lower ranges wherein the sum aggregate of isophthalic acid, benzoic acid, 4-carboxybenzaldehyde, and terephthalic acid have a lower range of 5 wt %, 10 wt %, 15 wt %, 20 wt %, 25 wt %, 30 wt %, 35 wt %, 40 wt % and a upper range of 65 wt %, 60 wt %, 55 wt %, 50 wt %, 45 wt % based on the total weight of the aqueous mixture 307.

When separating in the solid-liquid separation zone 351 is performed, a small amount of extraction solvent in conduit 311, generally about 1 to about 10% by weight, preferably about 5% by weight, may be added to the mixing zone 348 to enhance slurry handling by reducing adherence of solids to the side of, for example, a slurry feed tank. This is represented by the dashed arrow from stream 311 in FIG. 1.

Step (d) comprises optionally separating organic impurities 312 from the aqueous mixture 307 in a solid-liquid separation zone 351 to form a purified aqueous mixture 308.

The aqueous mixture stream 307 can be optionally fed to a solid-liquid separation zone 351 comprising a solid-liquid apparatus, wherein organic impurities 312 may be removed from the aqueous mixture 307 to form a purified aqueous mixture 308 and organic impurities 312. There are no limitations on the type of solid-liquid separation apparatus as long as it is sufficient to remove organic impurities 312 from the aqueous mixture 307. Examples of such apparatuses include, but are not limited to, filters, centrifuges, cyclones, hydroclones, etc.

The organic impurities can comprise numerous compounds typically associated with TPA production. Examples of typical organic impurities include, but are not limited to, isophthalic acid, trimellitic acid, benzoic acid, phthalic acid, fluorenones compounds, p-toluic acid, and 4-carboxybenzaldehyde.

In one embodiment, a typical composition of the purified aqueous mixture 308 is shown in Table 1. The mass composition of the purified aqueous mixture 308 in this embodiment comprises acetic acid, water, isophthalic acid, benzoic acid, 4-carboxybenzaldehyde, terephthalic acid, and cobalt; wherein the sum aggregate of the isophthalic acid, benzoic acid, 4-carboxybenzaldehyde, and terephthalic acid comprise between about 1 wt % to 70% based on the total weight of the purified aqueous mixture 308; wherein the sum aggregate of isophthalic acid and terephthalic acid comprise no more than 10 wt % of the purified aqueous mixture 308. Another range can be all combinations of upper and lower ranges wherein the sum aggregate of isophthalic acid, benzoic acid, 4-carboxybenzaldehyde, and terephthalic have a lower range of 5 wt %, 10 wt %, 15 wt %, 20 wt %, 25 wt %, 30 wt %, 35 wt %, 40 wt % based on the total weight of the purified aqueous mixture 308 and a upper range of 65 wt %, 60 wt %, 55 wt %, 50 wt %, 45 wt % based on the total weight of the purified aqueous mixture 308; and wherein the sum aggregate of isophthalic acid and terephthalic acid comprise no more than 10 wt % based on the total weight of the purified aqueous mixture 308.

As previously stated when the solid-liquid separation zone 351 is utilized, a small amount of extraction solvent in conduit 311, generally about 1 to about 10% by weight, preferably about 5% by weight may be added to the mixing zone 348 to enhance slurry handling by reducing adherence of solids to the side of, for example, a slurry feed tank. This is represented by the dashed arrow from stream 311 in FIG. 1.

Step (e) comprises adding an extraction solvent 311 to the aqueous mixture 307 or the purified aqueous mixture 308 in an extraction zone 323 to form an extract stream 309 and the raffinate stream 310.

The aqueous mixture 307 or the purified aqueous mixture 308 is fed to an extraction zone 323 wherein the aqueous mixture 307 or the purified aqueous mixture 308 and the extraction solvent 311 are contacted in the extraction zone 323. The aqueous mixture 307 or the purified aqueous mixture 308 and the extraction solvent 311 are mixed to form an extract stream 309 comprising solvent, water organic impurities, and organic solvent which forms a lighter phase, and the raffinate stream 310 comprising a metal catalyst, corrosion metals, and water. The extract stream 309 is withdrawn as an overhead stream, and the raffinate stream 310 is withdrawn from the bottom of extractor in the extraction zone 323. In this invention, one embodiment of the extraction zone 323 is a single stage extractor.

The extraction solvent 311 used in the extractor should be substantially water-insoluble to minimize the amount of organic solvent dissolved in the aqueous fraction. Additionally, the extraction solvent 311 is preferably an azeotropic agent which serves to assist solvent recovery from the organic extract. Solvents, which have proven to be particularly useful are C1 to C6 alkyl acetates, particularly n-propyl acetate (n-PA), isopropyl acetate, isobutyl acetate, sec-butyl acetate, ethyl acetate and n-butyl acetate, although other water-insoluble organic solvents having an appropriate density and a sufficiently low boiling point may also be used, such as p-xylene. N-propyl acetate and isopropyl acetate are particularly preferred due to their relatively low water solubility, excellent azeotropic behavior, and their ability to remove the remaining acetic acid as well as high-boiling organic impurities from the aqueous mixture.

The extraction can be effected using extraction solvent ratios from about 1 to about 4 parts by weight extraction solvent per part of extractor feed depending on the extractor feed composition. Space velocities of the combined feeds to the extractor generally range from about 1 to about 3 $hr^{-1}$. Although the extraction can be conducted at ambient temperature and pressure, heating the extraction solvent 311 and extractor to about 30° to about 70° C. Another range of about 40° C. to about 60° C. can be used. Although the extract stream 309 comprises small amounts of the metal catalyst and corrosion metals, essentially all of the metal catalyst and the majority of the remaining corrosion metals are contained in the heavier phase, the raffinate stream 310.

Step (f) comprises separating the extract stream 309 and the solvent rich stream 344 in a separation zone 324 to form a high boiling point organic impurities stream 315.

The extract stream 309 comprises organic solvent and organic impurities. The extract stream 309 can further comprises acetic acid and water, often in minor amounts. The extract stream 309 may be distilled in a separation zone comprising conventional distillation equipment. The distillation equipment is operated at process conditions sufficient to recover a majority of the extraction solvent, typically n-propyl acetate, from the extract stream 309. Convention distillation equipment includes, for example, a distillation column. One key feature to this invention is the use of the solvent rich stream 344 into the separation zone 324.

Most of the organic impurities are extracted by the organic solvent in the extraction zone 323. This occurs because the organic impurities show a high degree of solubility for the organic solvent and to a lesser extent for acetic acid. By distilling the lighter phase from the extractor, the organic solvent is evaporated allowing the organic impurities to concentrate in the column underflow. This results in a high probability for plugging and precipitation of solids. By utilizing the solvent rich stream 344, the organic impurities in the column underflow can be effectively diluted and thereby solubilized by acetic acid in the column underflow.

The use of the solvent rich stream 344, from the previous evaporation serves two functions. First, the loss of the organic solvent is minimized since the solvent rich stream 344 effectively displaces the organic solvent in the column underflow. Second, the use of acetic-acid rich vapor provides significant enthalpy needed for driving the distillation/separation process.

The separation zone 324 will need to process significantly less hydraulic load than a typical purge process due to the greater concentration of mother liquor. Recovered extraction solvent and acetic acid may be recycled to the extractor and oxidative reactor, respectively. The high-boiling point organic impurities are removed as sludge from the base of the distillation column for disposal.

Although the composition of the various streams in the process varies depending on the process conditions, a typical composition of the streams are shown in Table 1. In Table 1, the components are shown in the left hand column and the amount of these components in each stream in the FIG. 1 are shown in the number column corresponding to the number of the stream in FIG. 1. The amounts of the components shown in Table 1 can be any measurement of weight as long as it is consistent for all components and all streams. For example, the oxidizer purge stream 301 has acetic acid in the amount of 915 pounds, 915 grams, etc.

TABLE 1

Material Balance

Process Material Balance Stream in FIG. 1

| | 301 | 304 | 305 | 344 | 345 | 306 | 307 | 308 | 309 | 310 | 311 | 312 |
|---|---|---|---|---|---|---|---|---|---|---|---|---|
| Acetic Acid | 915.0 | 534.1 | 380.9 | 335.2 | 45.8 | — | 45.8 | 45.3 | 44.1 | 1.2 | — | 0.4 |
| Water | 55.0 | 39.3 | 15.7 | 14.7 | 1.0 | 80.0 | 81.0 | 80.2 | 35.6 | 44.5 | — | 0.7 |
| n-Propyl Acetate | — | — | — | — | — | — | — | — | 399.0 | 1.0 | 400.0 | — |
| Terephthalic Acid | 0.71 | — | 0.71 | — | 0.71 | — | 0.71 | 0.70 | 0.70 | — | — | — |
| Isophthalic Acid | 5.83 | — | 5.83 | — | 5.83 | — | 5.83 | 5.78 | 5.71 | 0.07 | — | 0.05 |
| Phthalic Acid | 3.81 | — | 3.81 | 0.12 | 3.69 | — | 3.69 | 3.66 | 3.36 | 0.29 | — | 0.03 |
| Benzoic Acid | 8.12 | 0.06 | 8.06 | 2.27 | 5.79 | — | 5.79 | 5.73 | 5.73 | — | — | 0.05 |
| 4-Carboxybenzaldehyde | 1.56 | — | 1.56 | — | 1.56 | — | 1.56 | 1.54 | 1.52 | 0.02 | — | 0.01 |
| Trimellitic Acid | 1.17 | — | 1.17 | — | 1.17 | — | 1.17 | 1.16 | 1.01 | 0.14 | — | 0.01 |
| Paratoluic Acid | 2.96 | 0.01 | 2.95 | 0.50 | 2.44 | — | 2.44 | 2.42 | 2.39 | 0.03 | — | 0.02 |
| Paratolualdehyde | 0.51 | 0.05 | 0.46 | 0.26 | 0.20 | — | 0.20 | 0.20 | 0.20 | — | — | — |
| Others | 2.50 | — | 2.50 | — | 2.50 | — | 2.50 | 2.38 | 2.14 | 0.24 | — | 0.13 |
| Organic Bromide | 1.30 | — | 1.30 | — | 1.30 | — | 0.90 | 0.86 | — | 0.85 | — | 0.05 |
| Ionic Bromide | 0.34 | — | 0.34 | — | 0.34 | — | 0.74 | 0.70 | — | 0.70 | — | 0.04 |
| Cobalt | 1.44 | — | 1.44 | — | 1.44 | — | 1.44 | 1.37 | 0.01 | 1.35 | — | 0.07 |
| Manganese | 0.10 | — | 0.10 | — | 0.10 | — | 0.10 | 0.10 | — | 0.09 | — | — |
| Corrosion Metals | 0.08 | — | 0.08 | — | 0.08 | — | 0.08 | 0.08 | — | 0.08 | — | — |
| Total | 1000 | 573 | 427 | 353 | 74 | 80 | 154 | 152 | 502 | 51 | 400 | 2 |

*The amounts of the components shown in Table 1 can be any measurement of weight as long as it is consistent for all components and all streams

We claim:

1. A process comprising:
   (a) subjecting an oxidizer purge stream comprising a carboxylic acid, a metal catalyst, impurities, water and a solvent to evaporation in a first evaporator zone to produce a vapor stream and a concentrated purge slurry; and
   (b) subjecting said concentrated purge slurry to evaporation in a second evaporator zone to produce a solvent rich stream and a high temperature molten dispersion; wherein about 95 wt % to about 99 wt % of said solvent and water present in said oxidizer purge stream from step (a) is removed and wherein said second evaporator zone comprises an evaporator operated at a temperature of about 150° C. to about 200° C.;
   (c) mixing in a mixing zone a wash solution with said high temperature molten dispersion to form an aqueous mixture;
   (d) adding an extraction solvent to said aqueous mixture in an extraction zone to form an extract stream and a raffinate stream; and
   (e) separating said extract stream and said solvent rich stream in a separation zone to form a high boiling point organic impurities stream.

2. The process according to claim 1 wherein a wash solution is added to quench said aqueous mixture to a temperature range of about 60° C. to about 95° C.

3. The process according to claim 1 wherein a said wash solution is added to quench said aqueous mixture to a temperature range of 80° C. to about 90° C.

4. The process according to claim 1 wherein said extraction zone comprises a counter current extractor.

5. The process according to claim 1 wherein said extraction zone comprises a single stage extractor.

6. The process according to claim 1 wherein said solvent rich stream comprises a solvent selected from the group consisting of n-propyl acetate, isopropyl acetate, isobutyl acetate, sec-butyl acetate, ethyl acetate, n-butyl acetate and mixtures thereof.

7. The process according to claim 6 wherein said second evaporator zone comprises an evaporator operated at a pressure of 1 atmosphere to about 10 atmospheres.

8. A process comprising:
   (a) subjecting an oxidizer purge stream comprising a carboxylic acid, a metal catalyst, impurities, water and a solvent to evaporation in a first evaporator zone to produce a vapor stream and a concentrated purge slurry; and
   (b) subjecting said concentrated purge slurry to evaporation in a second evaporator zone to produce a solvent rich stream and a high temperature molten dispersion; wherein about 95 WT % to about 99 wt % of said solvent and water present in said oxidizer purge stream from step (a) is removed; and wherein said second evaporator zone comprises an evaporator operated at a temperature of about 150° C. to about 200° C.;
   (c) mixing in a mixing zone a wash solution with said high temperature molten dispersion to form an aqueous mixture;
   (d) separating organic impurities from said aqueous mixture in a solid-liquid separation zone to form a purified aqueous mixture;
   (e) adding an extraction solvent to purified aqueous mixture in an extraction zone to form an extract stream and a raffinate stream; and
   (f) separating said extract stream and said solvent rich stream in a separation zone to form a high boiling point organic impurities stream.

9. The process according to claim 8 wherein said a wash solution is added to quench said aqueous mixture to a temperature range of about 600° C. to about 95° C.

10. The process according to claim 8 wherein a wash solution is added to quench said aqueous mixture to a temperature range of 80° C. to about 90° C.

11. The process according to claim 8 wherein said extraction zone comprises a counter current extractor.

12. The process according to claim 8 wherein said extraction zone comprises a single stage extractor.

13. The process according to claim 8 wherein said solvent rich stream comprises a solvent selected from the group consisting of n-propyl acetate, isopropyl acetate, isobutyl acetate, sec-butyl acetate, ethyl acetate, n-butyl acetate and mixtures thereof.

14. The process according to claim 13 wherein said second evaporator zone comprises an evaporator operated at a pressure of 1 atmosphere to about 10 atmospheres.

* * * * *

UNITED STATES PATENT AND TRADEMARK OFFICE
CERTIFICATE OF CORRECTION

PATENT NO. : 7,452,522 B2 Page 1 of 1
APPLICATION NO. : 10/948591
DATED : November 18, 2008
INVENTOR(S) : Lin et al.

It is certified that error appears in the above-identified patent and that said Letters Patent is hereby corrected as shown below:

Column 10, Line 57, Claim 9 "wherein said a" should read --wherein a--;
Column 10, Line 59, Claim 9 "600°" should read --60°--.

Signed and Sealed this

Thirteenth Day of January, 2009

JON W. DUDAS
*Director of the United States Patent and Trademark Office*